(12) United States Patent
Petersheim et al.

(10) Patent No.: US 10,543,104 B2
(45) Date of Patent: Jan. 28, 2020

(54) SPINAL PLATE

(71) Applicant: GLOBUS MEDICAL, INC., Audubon, PA (US)

(72) Inventors: Samuel Petersheim, Elverson, PA (US); Ryan Agard, Royersford, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 139 days.

(21) Appl. No.: 15/223,664

(22) Filed: Jul. 29, 2016

(65) Prior Publication Data
US 2016/0331549 A1    Nov. 17, 2016

Related U.S. Application Data

(63) Continuation of application No. 13/439,981, filed on Apr. 5, 2012, now Pat. No. 9,427,330, which is a
(Continued)

(51) Int. Cl.
*A61F 2/44*    (2006.01)
*A61B 17/80*    (2006.01)
(Continued)

(52) U.S. Cl.
CPC ........ *A61F 2/4455* (2013.01); *A61B 17/7059* (2013.01); *A61B 17/808* (2013.01); *A61B 17/809* (2013.01); *A61B 17/8042* (2013.01); *A61B 17/92* (2013.01); *A61F 2/447* (2013.01); *A61F 2/4611* (2013.01); *A61B 2017/922* (2013.01); *A61F 2002/308* (2013.01);
(Continued)

(58) Field of Classification Search
CPC ...... A61F 2/4611; A61F 2/447; A61F 2/4455; A61F 2002/4475; A61F 2002/4622; A61F 2002/4635
See application file for complete search history.

(56) References Cited

U.S. PATENT DOCUMENTS 2,133,859 A    10/1938 Hawley
3,352,190 A    11/1967 Carlson
(Continued)

FOREIGN PATENT DOCUMENTS

JP    6-277228    10/1994
JP    2004-500156    1/2004
(Continued)

*Primary Examiner* — Ellen C Hammond

(57) ABSTRACT

Spinal plates with additional features to improve the stability of the interface between the plate and the underlying bone. A bone plate may include one or more sharp ridges along the periphery of its underside. When attached to bone, the ridge digs into the bone and increases stability. A bone plate may alternatively or additionally include one or more holes for optional spikes, which may be inserted once the plate is attached to the bone. By separating the spikes and including them as an optional component, the plate may enhance stability while reducing or eliminating the chance of the spike injuring the patient. Furthermore, bone screws may incorporate alternating notches and ridges into the head of the screw. The notches and ridges may interface with a set screw, thereby preventing rotation and loosening of the screw.

12 Claims, 12 Drawing Sheets

Related U.S. Application Data continuation-in-part of application No. 13/226,092, filed on Sep. 6, 2011.

(51) Int. Cl.

| | | |
|---|---|---|
| *A61B 17/70* | (2006.01) | |
| *A61B 17/92* | (2006.01) | |
| *A61F 2/46* | (2006.01) | |
| *A61F 2/30* | (2006.01) | |

(52) U.S. Cl.
CPC ............ *A61F 2002/3098* (2013.01); *A61F 2002/30433* (2013.01); *A61F 2002/30482* (2013.01); *A61F 2002/30509* (2013.01); *A61F 2002/30576* (2013.01); *A61F 2002/30578* (2013.01); *A61F 2002/30607* (2013.01); *A61F 2002/30772* (2013.01); *A61F 2002/30785* (2013.01); *A61F 2002/30787* (2013.01); *A61F 2002/30843* (2013.01); *A61F 2002/30904* (2013.01); *A61F 2002/4475* (2013.01); *A61F 2002/4615* (2013.01); *A61F 2002/4622* (2013.01); *A61F 2220/0016* (2013.01); *A61F 2310/00407* (2013.01); *A61F 2310/00796* (2013.01)

(56) References Cited

U.S. PATENT DOCUMENTS

| | | | |
|---|---|---|---|
| 5,888,223 A | 3/1999 | Bray, Jr. | |
| 6,193,721 B1 | 2/2001 | Michelson | |
| 6,228,085 B1 | 5/2001 | Theken et al. | |
| 6,235,059 B1 | 5/2001 | Benezech et al. | |
| 6,576,017 B2 | 6/2003 | Foley et al. | |
| 6,746,450 B1 | 6/2004 | Wall et al. | |
| 7,594,931 B2 | 9/2009 | Louis et al. | |
| 7,815,681 B2 | 10/2010 | Ferguson | |
| 8,480,747 B2* | 7/2013 | Melkent | A61F 2/442 623/17.11 |
| 8,500,811 B2 | 8/2013 | Blain et al. | |
| 8,945,227 B2 | 2/2015 | Kirschman | |
| 8,956,416 B2* | 2/2015 | McCarthy | A61F 2/4455 623/17.16 |
| 9,186,257 B2 | 11/2015 | Geisler et al. | |
| 2001/0020185 A1 | 9/2001 | Ray | |
| 2004/0116930 A1 | 6/2004 | O'Driscoll et al. | |
| 2004/0126407 A1 | 7/2004 | Falahee | |
| 2004/0127901 A1 | 7/2004 | Huebner et al. | |
| 2005/0065605 A1 | 3/2005 | Jackson | |
| 2005/0143822 A1* | 6/2005 | Paul | A61F 2/4455 623/17.16 |
| 2005/0159813 A1 | 7/2005 | Molz, IV | |
| 2005/0187551 A1 | 8/2005 | Orbay et al. | |
| 2005/0261690 A1 | 11/2005 | Binder et al. | |
| 2006/0106387 A1 | 5/2006 | Fanger et al. | |
| 2008/0294262 A1* | 11/2008 | Levieux | A61F 2/447 623/17.16 |
| 2009/0012529 A1* | 1/2009 | Blain | A61B 17/7059 606/99 |
| 2009/0012570 A1 | 1/2009 | Zhang et al. | |
| 2009/0198245 A1 | 8/2009 | Phan | |
| 2010/0100138 A1 | 4/2010 | Reynolds et al. | |
| 2010/0121382 A1 | 5/2010 | Weiman | |
| 2011/0022097 A1 | 1/2011 | Walker et al. | |
| 2011/0087229 A1 | 4/2011 | Kubiak et al. | |
| 2011/0190892 A1* | 8/2011 | Kirschman | A61F 2/44 623/17.16 |
| 2012/0143336 A1* | 6/2012 | Aflatoon | A61F 2/4465 623/17.16 |
| 2012/0245690 A1* | 9/2012 | Cowan, Jr. | A61F 2/4465 623/17.16 |
| 2012/0277865 A1* | 11/2012 | Trieu | A61F 2/442 623/17.16 |
| 2013/0060337 A1 | 3/2013 | Petersheim et al. | |
| 2015/0100126 A1* | 4/2015 | Melkent | A61F 2/4455 623/17.16 |

FOREIGN PATENT DOCUMENTS

| | | |
|---|---|---|
| JP | 2008-520272 | 6/2008 |
| WO | 200103570 A2 | 1/2001 |
| WO | 2010008593 A1 | 1/2010 |

* cited by examiner

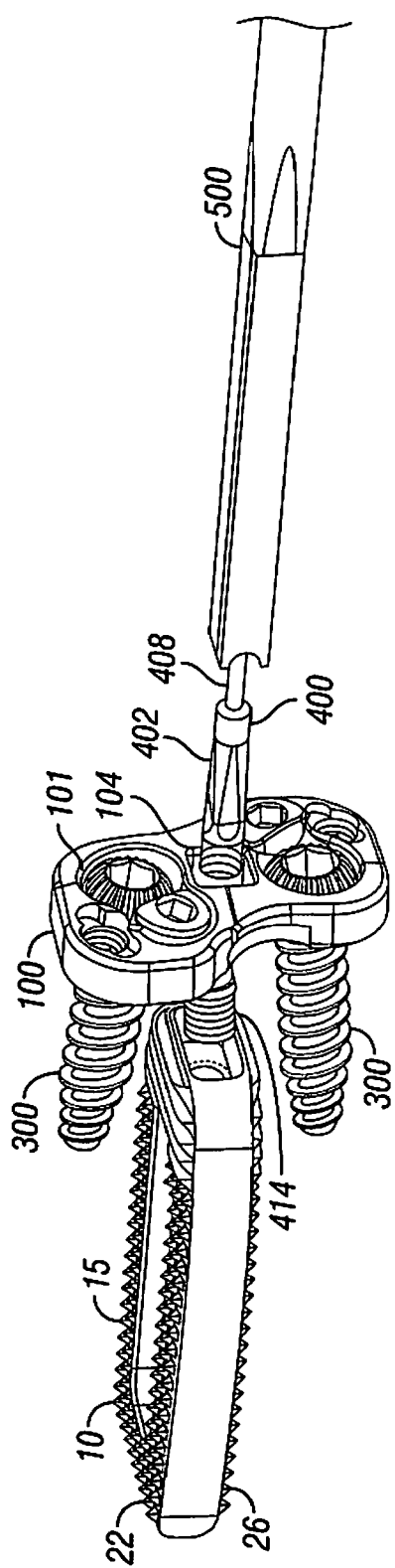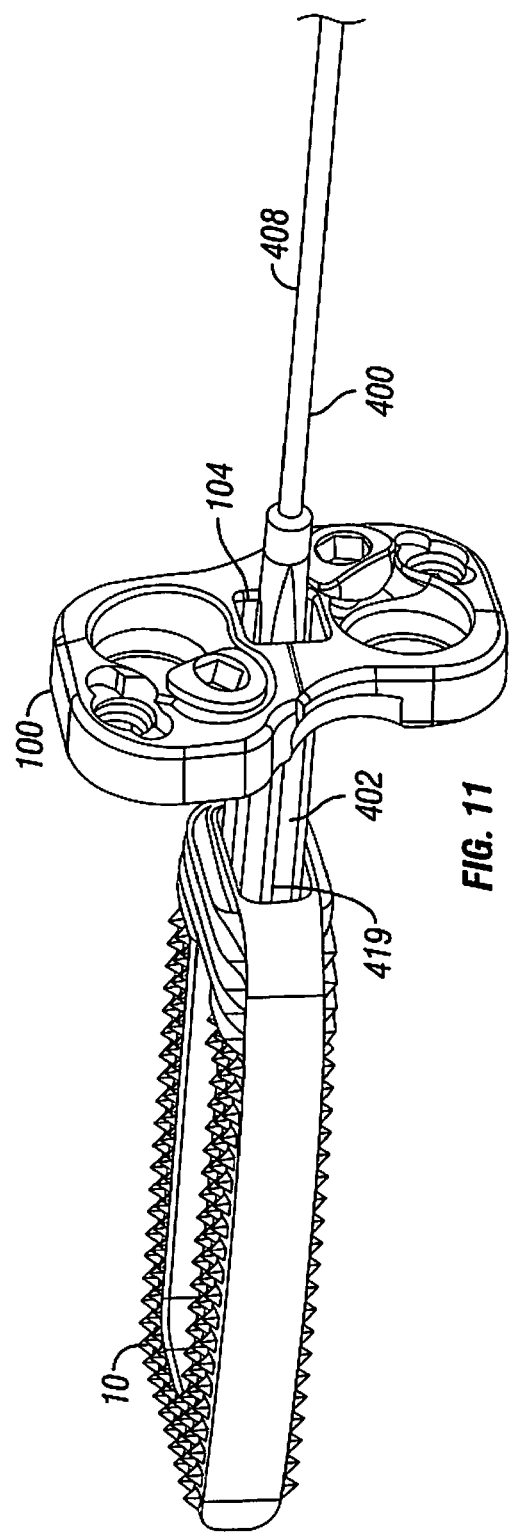

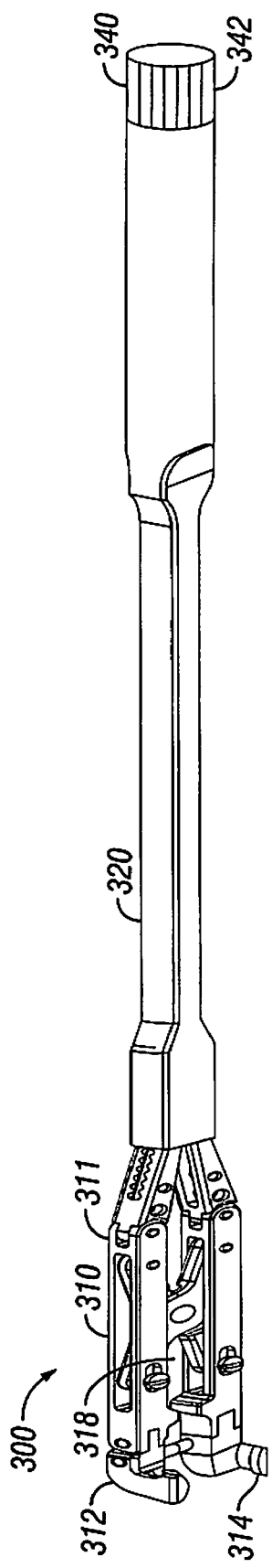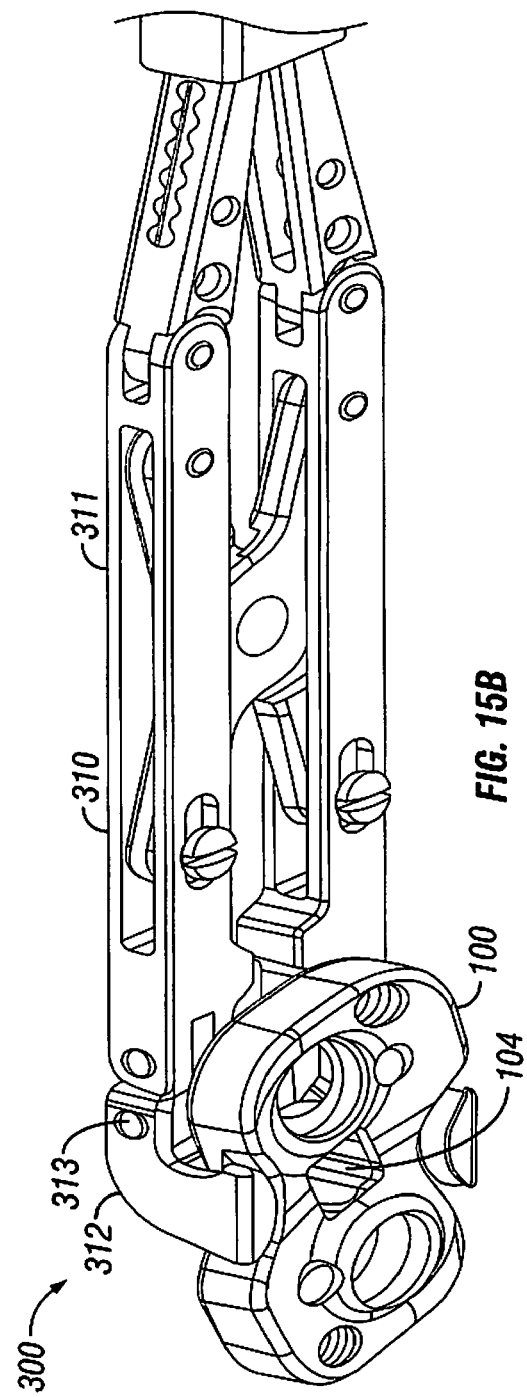
FIG. 15A
FIG. 15B

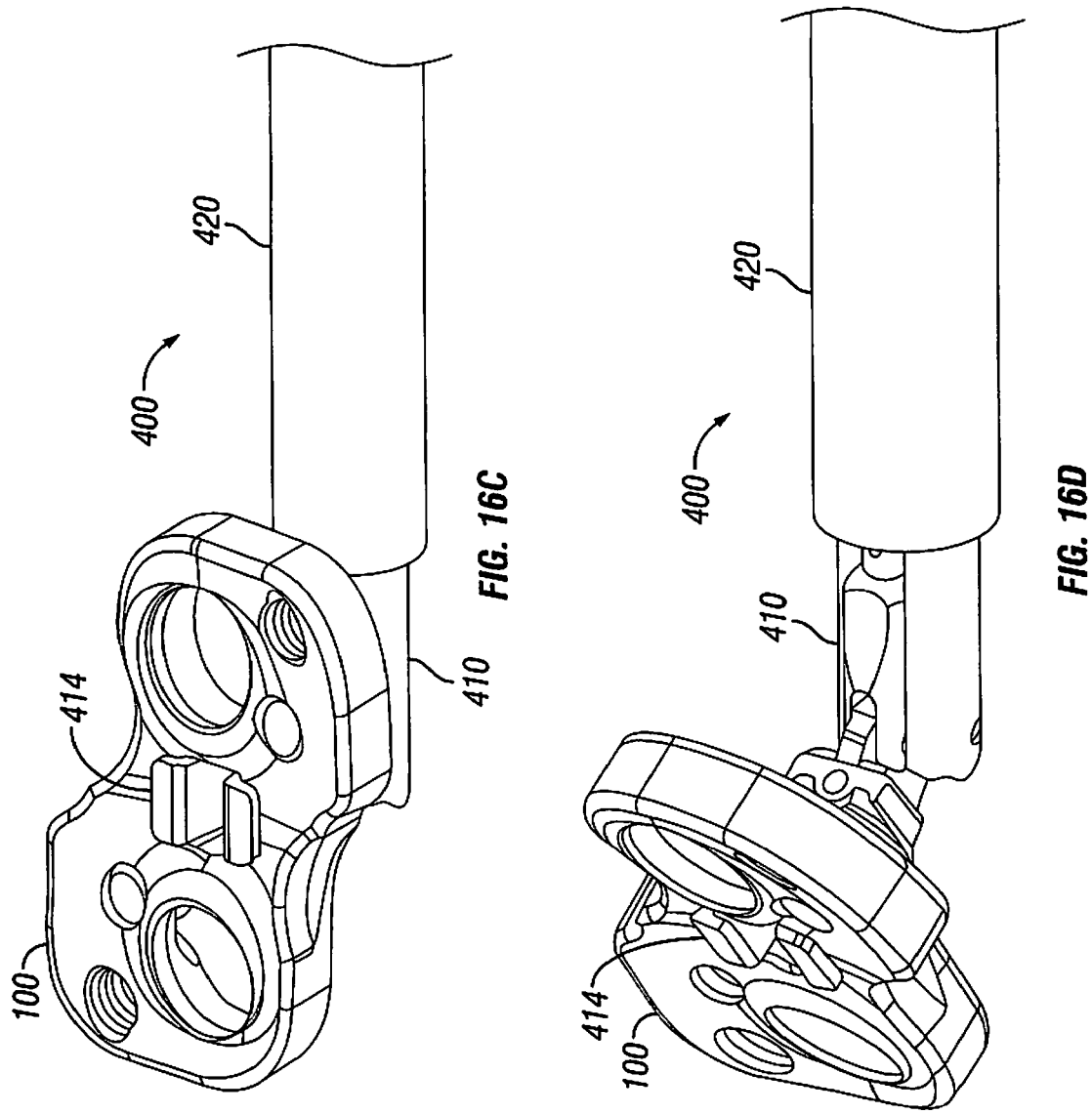

SPINAL PLATE

CROSS REFERENCE TO RELATED APPLICATIONS

This application is a continuation application of U.S. patent application Ser. No. 13/439,981, filed on Apr. 5, 2012, which is a continuation-in-part application of U.S. patent application Ser. No. 13/226,092, filed on Sep. 6, 2011, each of which is incorporated by reference herein in its entirety.

BACKGROUND OF THE DISCLOSURE

1. Field of the Disclosure

The disclosure relates to devices for immobilizing two or more vertebrae relative to one another to promote fusion of the vertebrae. The devices and improvements described herein may also be used with other types of bone plates or instrumentation.

2. Related Art

Adjacent vertebrae may be surgically joined together in a fusion procedure. The procedure may join two (bi-level) or more (multi-level) vertebrae. During the surgery, the vertebrae are fixed in position relative to one another with a plate or other instrumentation, and a bone graft is placed between the vertebrae. The bone graft will promote new bone growth between the vertebrae, and eventually the bones will grow together, which typically takes 6-18 months after the surgery.

More commonly, fusion of vertebrae is used as part of a treatment for a herniated disc, rheumatoid arthritis, infection, tumor, or other condition resulting in spinal deformities. In each case, the primary disease is treated before the fusion procedure. In the case of a herniated disc or degenerative disc disorder, for example, the intervertebral disc is removed (a procedure known as a discectomy). After the discectomy, the instrumentation is attached to the vertebrae. The two related procedures are typically performed as part of the same surgery, to minimize trauma and expense to the patient.

Many devices are available for instrumentation of the spine in a fusion procedure. Current spinal plates, however, suffer from one or more limitations. For example, there are often situations and size restrictions that limit the number of screws that can be used in a design or surgery. Fewer screws results in lower stability of the plate.

One solution to this problem has been to add spikes or other sharp features to the plate. The spikes increase the stability of the bone-plate interface, as well as the stability of the underlying bone structures. There is a risk, however, that the sharp features may puncture or damage blood vessels, nerves, or other delicate anatomical structures during placement. There is also a difficulty for the surgeon to determine how well the plate will rest on the bone surface without first inserting the spikes into the bone.

Spinal plates are commonly fixed to bone with bone screws. Many modern plate designs incorporate blocking set screws, which prevent the bone screws from backing out of the bone after they have been implanted. Blocking set screws, however, do not prevent the bone screws from rotating. It is possible for the bone screws to rotate and loosen while they are held in place by the set screws. Loose bone screws reduce the stability of the bone-plate interface, thereby reducing the chance of a successful fusion procedure.

Accordingly, there is a need for a bone plate that provides enhanced stability and prevents rotation of the bone screws holding the plate to the bone.

SUMMARY OF THE DISCLOSURE

The disclosure meets the foregoing need and allows increased safety and/or stability using advanced bone plates, which results in a significant increase in positive patient outcomes and other advantages apparent from the discussion herein.

Various systems, devices and methods are provided that relate to vertebral fusion. In some embodiments, a surgical method comprises inserting a spacer body into a disc space; operably connecting a guide member to the spacer body; passing a plate over the guide member to position the plate adjacent the spacer body, wherein the plate includes at least one hole to receive a fastener; and securing the plate to a vertebral body by inserting at least one fastener through the at least one hole of the plate into the vertebral body.

In some embodiments, a surgical method comprises inserting a spacer body into a disc space; operably connecting a guide member to the spacer body, wherein the guide member comprises a first portion and a second portion, the second portion being more flexible than the first portion; passing a plate over the guide member to position the plate adjacent the spacer body; and securing the plate to a vertebral body.

In some embodiments, a surgical method comprises inserting a spacer body into a disc space, wherein the spacer body includes a recess; operably connecting a guide member adjacent to the spacer body; passing a plate over the guide member to position the plate adjacent the spacer body; and securing the plate to a vertebral body.

Additional features, advantages, and aspects of the disclosure may be set forth or apparent from consideration of the following detailed description, drawings, and claims. Moreover, it is to be understood that both the foregoing summary of the disclosure and the following detailed description are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate aspects of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings:

FIG. 10 shows a system including a tool for aligning a bone plate with a spacer body.

FIG. 11 shows an alternative system including a tool for aligning a bone plate with a spacer body.

FIG. 15A shows a top perspective view of a plate insertion device for delivering a plate to a desired location adjacent the spine.

FIG. 15B shows a perspective view of a distal portion of the plate insertion device of FIG. 15A grasping a plate.

FIG. 16C shows a bottom perspective view of a distal portion of the plate insertion device of FIG. 16A grasping a plate.

FIG. 16D shows a bottom perspective view of a distal portion of the plate insertion device of FIG. 16A grasping a plate at an alternative angle.

DETAILED DESCRIPTION OF THE DISCLOSURE

Figure 1A:
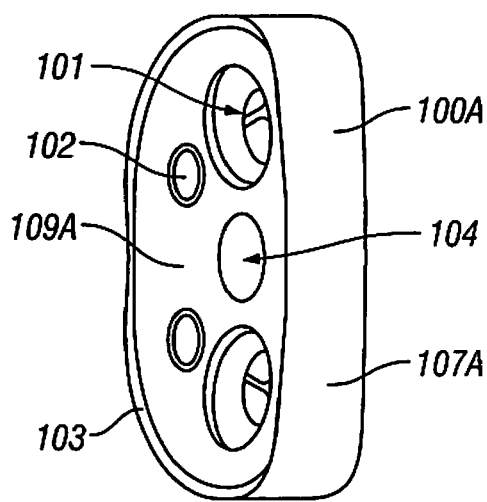
FIG. 1A shows a perspective view of an underside of a bone plate with a ridge that is flush with the sides of the bone plate.

The aspects of the disclosure and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one aspect may be employed with other aspects as the skilled artisan would recognize, even if not explicitly stated herein. Descriptions of well-known components and processing techniques may be omitted so as to not unnecessarily obscure the aspects of the disclosure. The examples used herein are intended merely to facilitate an understanding of ways in which the disclosure may be practiced and to further enable those of skill in the art to practice the aspects of the disclosure. Accordingly, the examples and aspects herein should not be construed as limiting the scope of the disclosure, which is defined solely by the appended claims and applicable law. Moreover, it is noted that like reference numerals represent similar parts throughout the several views of the drawings.

The terms "including", "comprising" and variations thereof, as used in this disclosure, mean "including, but not limited to", unless expressly specified otherwise.

The terms "a", "an", and "the", as used in this disclosure, mean "one or more", unless expressly specified otherwise.

Although process steps, method steps, algorithms, or the like, may be described in a sequential order, such processes, methods and algorithms may be configured to work in alternate orders. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

An incision, which may be no more than, e.g., about two inches long, may be made in a patient to perform a fusion of adjacent vertebrae. All instrumentation should pass through this incision, which naturally limits the size of bone plates and other hardware that may be used in the procedure. In certain situations, this size restriction can result in the use of a plate with a suboptimal amount of bone screws. Screws may be omitted due to difficulties in inserting the screws and other hardware through the incision. In other situations, the plate itself may only accept a suboptimal number of screws. Adding an optimal number of holes may make the plate too big to fit through the incision or otherwise satisfy space restrictions. Other situations and circumstances may also limit the number of screws used to attach a bone plate.

FIGS. 1A-4C and 7 show various examples of a bone plate 100 (100A, 100B, 100C, 100D, 100E) that may be implemented in spine fusion procedures to provided added stability in, e.g., the afore-noted situations. The bone plate 100 includes side walls 107 (107A, 107B), a top surface 108 (108A, 108B, 108C, 108D), and a bottom surface 109 (109A, 109B, 109C, 109D). The bone plate 100 may include one or more holes 101 that are configured to receive respective one or more bone screws (such as, e.g., the bone screw 300, shown in FIGS. 7-9B). The bone plate 100 may further include a central hole 104. The bone plate 100 may also include one or more receivers 110 that are configured to receive respective one or more set screws 102. The set screws 102 may help to retain the bone screws in the bone plate 100 and the bone (not shown), preventing the screws from loosening.

Figure 1B:
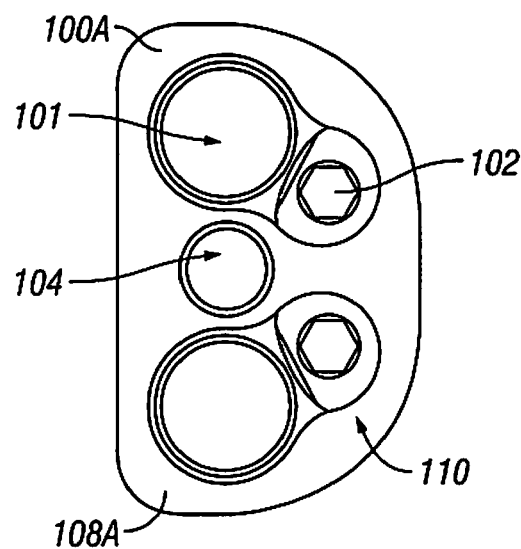
FIG. 1B shows a top-view of the bone plate of FIG. 1A.

Referring to FIGS. 1A-1B, the bone plate 100A may include a ridge 103A for added stability. The wall(s) of the ridge 103A may be tapered. The ridge 103A may be formed along (or near) a perimeter of the bone plate 100A. The ridge 103A may run along the entire perimeter of the bone plate 100A, or only a portion of the perimeter of the bone plate 100A. The bone plate 100A may be integrally formed with the ridge 103A. In particular, the bottom surface 109A of the bone plate 100A may be integrally formed with the ridge 103A.

FIG. 1A shows a perspective view of the underside, or bottom surface 109A, of the bone plate 100A, which is constructed with the ridge 103A being substantially flush with the side walls 107A of the bone plate 100A. The walls of the ridge 103A are tapered to form a substantially sharp edge along the perimeter of the ridge 103A.

FIG. 1B shows a view of the top surface 108A of the bone plate 100A. The ridge 103A is not visible in this top view, since the outer walls of the ridge 103A are substantially flush with the side walls 107A of the bone plate 100A.

Figure 2A:
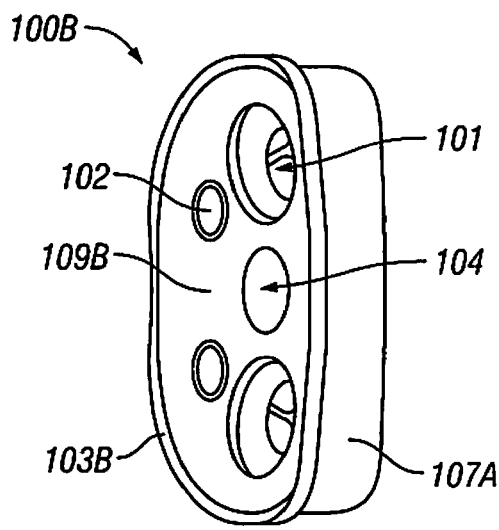
FIG. 2A shows a perspective view of a bone plate with a ridge that is located on a ring that extends past the outside edge of the bone plate.
Figure 2B:
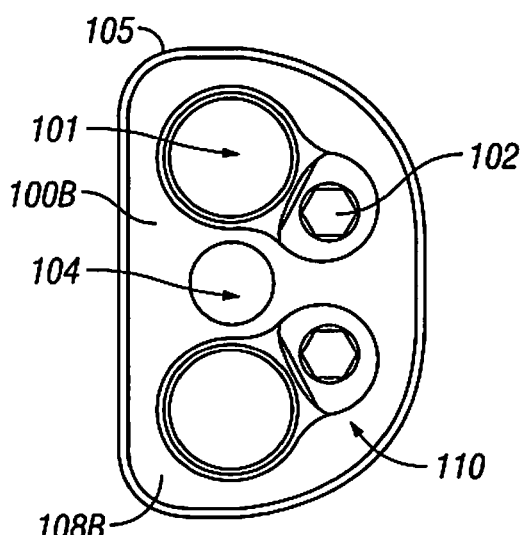
FIG. 2B shows a top-view of the bone-plate of FIG. 2A.

FIGS. 2A-2B show a bone plate 100B with a ring 105 and a ridge 103B, both of which may be integrally formed with the bone plate 100B. The ridge 103B may be formed on the ring 105, along the perimeter of the ring 105. The ring 105 may extend beyond the walls 107A of the bone plate 100B. The ring 105 may also extend beyond the bottom surface 109B of the bone plate 100B.

FIG. 2A shows a perspective view of the bottom surface 109B of the bone plate 100B, including the ridge 103B and the ring 105. As seen, the ridge 103B may include an inner wall that is configured to taper from the bottom surface 109B of the bone plate 100B (or the bottom surface of the ring 105) to the edge (or end) of the ridge 103B. Further, the ridge 103B may include an outer wall(s), which may be formed on the bottom surface of the ring 105, or which may be formed as part of the outer wall of the ring 105. The ring 105 may include an outer wall that may be substantially normal to the bottom surface 109B and substantially parallel to the walls 107A of the bone plate 100B. The outer wall of the ring 105 may be angled so as to taper off to an edge (or end) with the inner wall of the ridge 103B.

FIG. 2B shows a view of the top surface 108B of the bone plate 100B, including the ring 105. As seen, the ring 105 may be visible from the top view of the bone plate 100B.

Figure 3A:
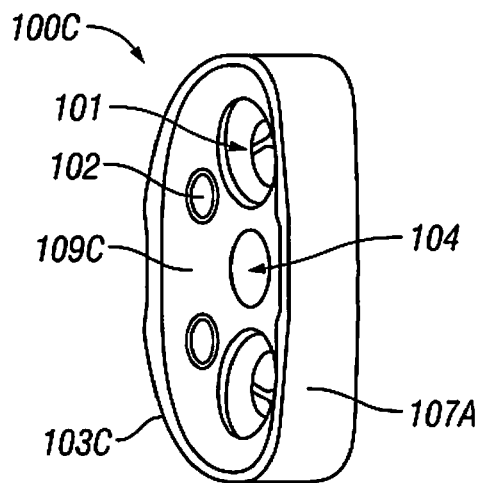
FIG. 3A shows a perspective view of a bone plate with a ridge that is inset from the outer edge of the plate.
Figure 3B:
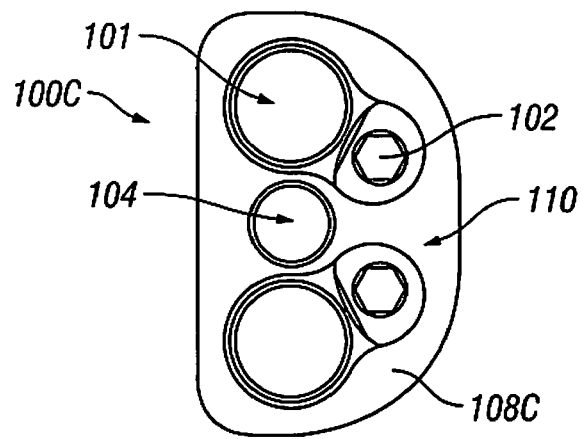
FIG. 3B shows a top-view of the bone plate of FIG. 3A.

FIGS. 3A-3B show a bone plate 100C with a ridge 103C that is formed inward of the perimeter of the bottom surface 109C. In particular, the ridge 103C is formed in the bone plate 100C so as to be inset from walls 107A of the bone plate 100C. One or both of the inner and outer walls of the ridge 103C may be tapered, so that wall(s) of ridge 103C taper off along a normal (or perpendicular) path from the bottom surface 109C to the edge (or end) of the ridge 103C.

FIG. 3A shows a perspective view of the bottom surface 109C, including the ridge 103C. As seen, the ridge 103C is inset from the walls 107A of the bone plate 100C.

FIG. 3B shows a view of the top surface 108C of the bone plate 100C. In this view, the ridge 103C is not visible.

While each of the figures shows only one ridge 103 (103A, 103B, 103C), those skilled in the art will recognize that multiple ridges 103 may be used without departing from the spirit or scope of the specification, including the attached claims. In particular, two or more ridges 103 may be used. For example, the ridge 103A of FIG. 1A may be combined with the ridge 103B of FIG. 2A to produce a bone plate 100 that includes a pair of ridges 103A, 103B (not shown). In addition, multiple ridges 103B may be located on the ring 105 shown in FIGS. 2A and 2B. The above is not an exhaustive list of the possible or contemplated examples, and further aspects will be apparent to those skilled in the art.

The inner wall and/or the outer wall of the ridge 103 (103A, 103B, 103C) may be tapered to a sharp edge (or end). The ridge 103 may also have a substantially sharp edge that is formed by substantially parallel inner and outer walls of the ridge 103 (not shown). Thus, by firmly attaching a bone plate 100 with a ridge 103 to, e.g., an underlying bone, using, e.g., a bone screw, the ridge 103 may contact and penetrate (or dig into) the bone. With the ridge 103 successfully implanted into the bone, lateral sliding of the bone plate 100 on the bone may be substantially or completed reduced or eliminated. The use of multiple ridges 103 may further enhance the anti-sliding effect of the ridges 103.

In addition, the ridge 103 may strengthen the bone-plate interface in additional ways. When the bone plate 100 is applied over multiple vertebrae, for example, the ridge 103 may work with the bone screws to prevent the vertebrae from moving relative to one another. Furthermore, the ridge 103 may be treated with a coating, such as, e.g., hydroxyapatite coating, titanium plasma spray, to encourage bony on-growth, which may stabilize or strengthen the interface between the plate and the underlying bone.

The improved stability imparted by a ridge 103 may have one or more effects on the use or design of the bone plate 100. As stated previously, the need for screws may be reduced. As a result, fewer screws may be used to secure the bone plate 100 to a bone, without compromising stability. Similarly, the size of the bone plate 100 may be reduced without a reduction in stability. A smaller bone plate 100 will likely require a smaller incision, which in turn may cause less trauma to the patient and improve recovery time.

Figure 4A:
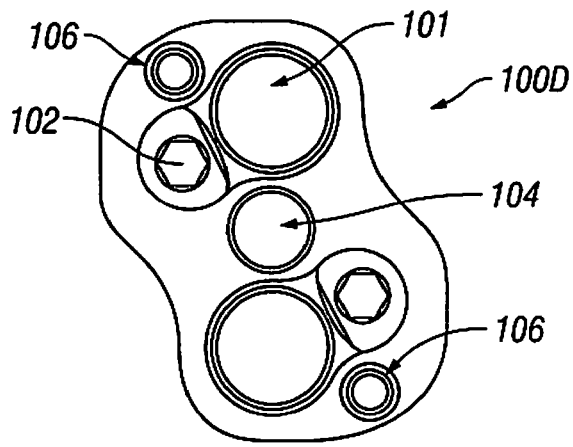
FIGS. 4A, 4B, and 4C show various views of a bone plate that is constructed to receive optional bone spikes.
Figure 4C:
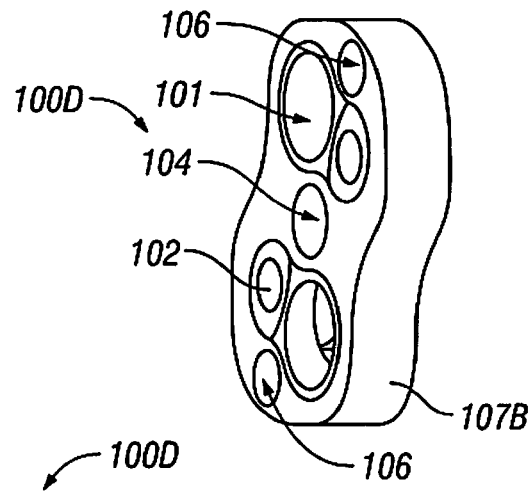
Figure 4B:
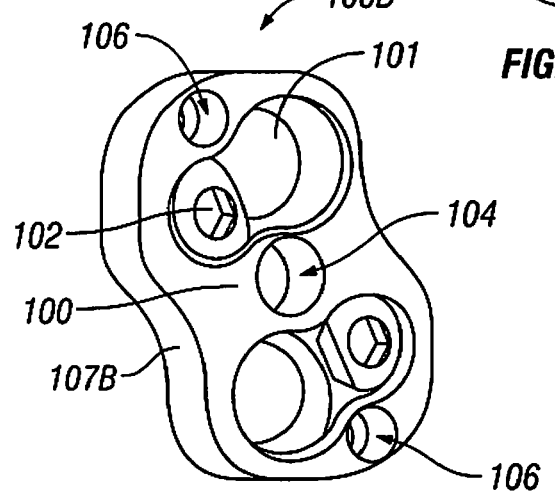

According to a further aspect of the disclosure, the bone plate 100 may include one or more sharp spikes to improve stability. The function of the spike is similar to that of the ridge 103 described above, but the spike may extend further away from the bone plate 100. FIGS. 4A, 4B, and 4C show various views of the bone plate 100D. The bone plate 100D is configured to receive one or more spikes. In particular, the bone plate 100D is configured to receive one or more optional spikes 206 that may be inserted in and through one or more respective openings 106 (in the bone plate 100D) and into, e.g., the bone (not shown). Once the bone plate 100D is securely attached to the bone with bone screws (e.g., the bone screws 300, shown in FIG. 7), one or more optional spikes 206 may be inserted through the spike holes 106 with a special tool 200 (shown in FIGS. 5A-6B).

Referring to FIGS. 5A-6B, the tool 200 includes a body 201, a plunger 202, and a shaft 203. The shaft 203 may run through the center and along the length of the body 201 and connect to the plunger 202 at a proximal end of the tool 200. The tool 200 is configured so that when the plunger 202 is depressed by, e.g., a surgeon, the shaft 203 is caused to move and extend from the distal end of the tool 200. Likewise, when the plunger 202 is in an extended position, the shaft 203 may be retracted from the distal end of the tool 200 by, e.g., a pulling force.

At the distal end of the tool 200, the shaft 203 may pass through a ring 204, which may act as a base for two or more panels 205. The distal end of the tool 200 may also be provided with slits. The interior of the panels 205 and the distal end of the shaft 203 may be designed in such a way that they close together, forming a continuous shape, when the plunger 202 is in a retracted position (i.e. when the plunger 202 is extended, shown in FIG. 5A). In addition, depressing the plunger 202 and extending the shaft 203 may cause the panels 205 to separate, as shown in FIG. 6B. For example, the distal end of the shaft 203 may have a tapered shape that presses against the interior walls of the panels 205 as the shaft 203 is extended.

The panels 205, the distal end of the shaft 203, or both may be configured to retain an optional spike 206 for use with the bone plate 100D shown in FIGS. 4A-4C. For example, the shaft 203 may be magnetized. In this instance, the shaft 203 may be used to pick up and easily retain a spike 206 that is manufactured from a ferromagnetic material. The panels 205 may contain an interior notch or ridge for gripping the spike 206 when the panels 205 are in a closed position. In addition, the panels 205 may be biased by a spring or other mechanism (not shown), enabling the panels 205 to grip the spike 206 with considerable force.

Figure 5A:
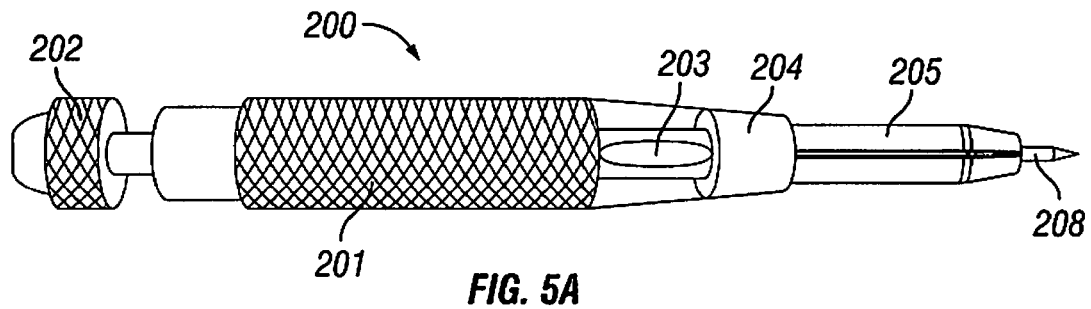
FIG. 5A shows a tool for inserting a spike into the plate shown in FIG. 4A with the plunger in an extended position.
Figure 5B:
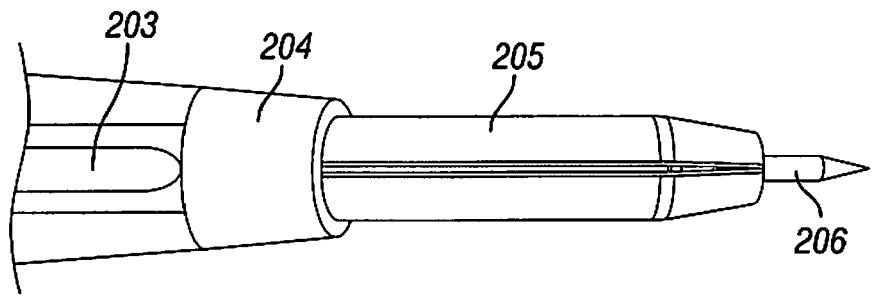
FIG. 5B shows a close-up view of the distal end of the tool of FIG. 5A.

FIG. 5A shows the spike tool 200 with the plunger 202 in an extended position. The distal end of the shaft 203 is retracted and the panels 205 are closed. The panels 205 are holding a spike 206 for use with the bone plate 100D shown in FIGS. 4A-4O. FIG. 5B provides a magnified view of the distal end of the tool 200, which shows an example of how the panels 205 may come together.

A tool 200 in this configuration may be used to insert a spike 206 through a spike hole 106 of the bone plate 100D. The hole 106 may be configured to mechanically engage and retain the spike 206 after it has passed a certain point. For example, the hole 106 may include a beveled ridge or ridges that allows the spike 206 to pass the ridge as it is inserted, yet prevents the spike 206 from working free of the hole 106. Additionally or alternatively, the hole 106 may include a ridge or notch that serves as a lower limit for the spike 206. In this instance, the spike may be prevented from being inserted through this ridge or notch. The limit ridge and the beveled ridge may work together to substantially fix the spike 206 in place, maximizing the spike's 206 contribution to the stability of the bone-plate interface and the overall construct.

Figure 6A:
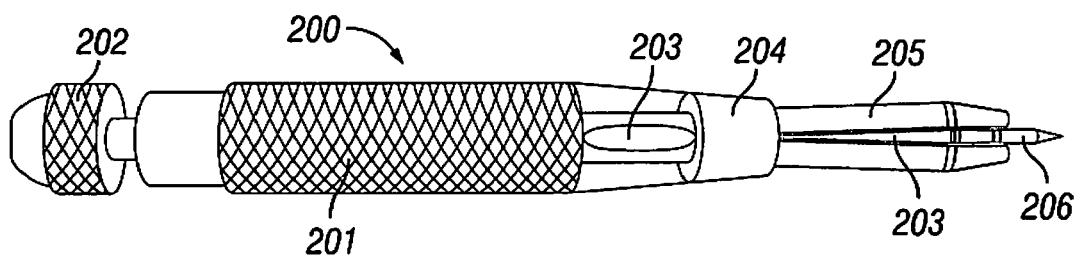
FIG. 6A shows a tool for inserting a spike into the plate shown in FIG. 4A with the plunger in a depressed position.
Figure 6B:
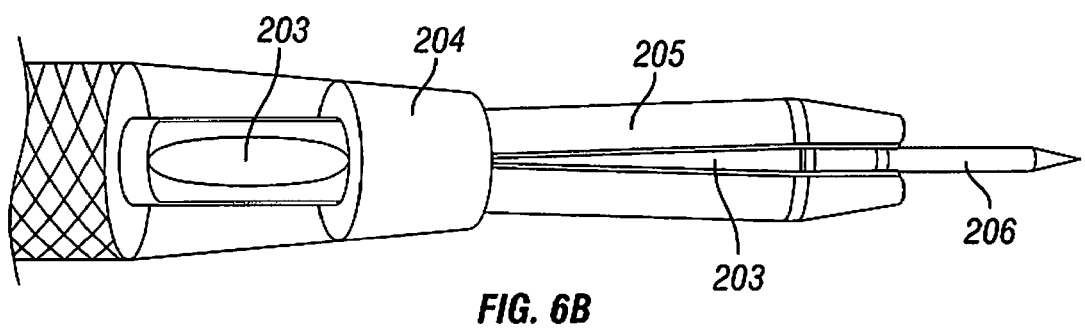
FIG. 6B shows a close-up view of the distal end of the tool of FIG. 6A.

FIG. 6A shows the tool 200 with the plunger 202 depressed and the shaft 203 extended. FIG. 6B shows a close-up of the distal end of the tool 200. Shaft 203 may force apart or separate the panels 205 while the tool 200 still retains the spike 206.

A bone plate 100D with optional spikes eliminates sharp protrusions from the plate that may injure blood vessels, nerves, and other anatomical features. In addition, the bone plate 100D may be used without some or all of the optional spikes 206 being inserted. This may allow surgeons or hospitals to reduce the number and type of bone plates 100 they keep in stock, thereby reducing costs.

Figure 7:
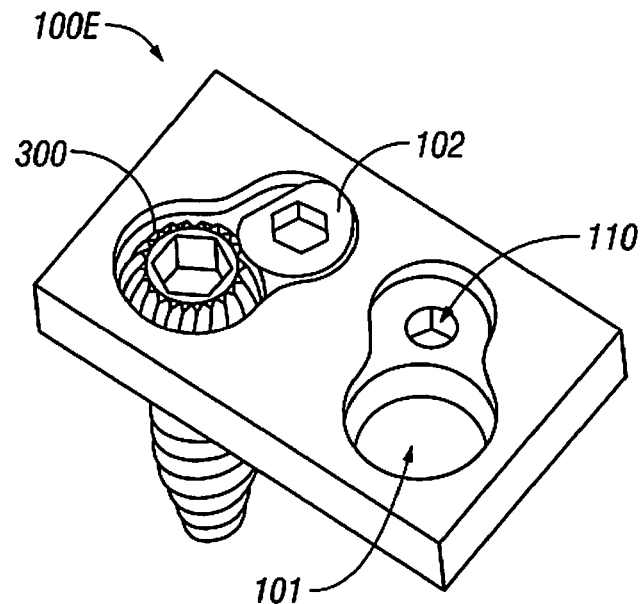
FIG. 7 shows a bone screw with a notched head.

FIG. 7 shows an example of a bone screw 300 that is constructed according to the principles of the disclosure. The bone screw 300 may include a notched head. The bone screw 300 may be used with a bone plate 100E. The bone plate 100E may be configured as any one of the bone plates 100A-100D previously described. The bone screw 300 may be used with a set screw 102 to prevent the bone screw 300 from working out of the underlying bone (not shown). As seen in FIG. 7, the bone plate 100E may include a hole 101 for receiving the bone screw 300 and a receiver 110 (such as, e.g., a hole) for receiving the set screw 102.

Figure 8:
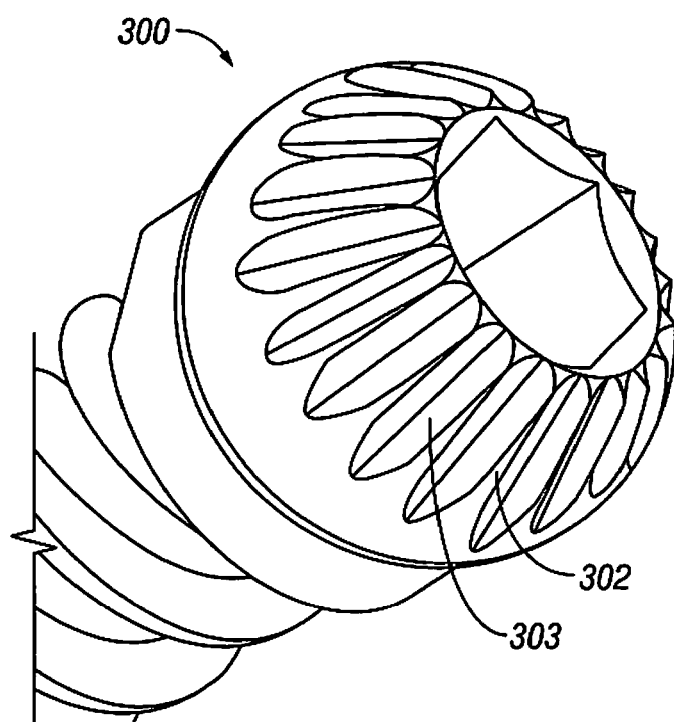
FIG. 8 shows a close-up view of the bone screw of FIG. 7.

FIG. 8 provides a close-up view of the head portion of the bone screw 300. The head portion of the bone screw 300 may include alternating ridges 302 and notches 303. This arrangement allows the set screw 102 to physically engage the head of the bone screw 300, thereby preventing both rotation and backing out of the bone screw 300 from the bone or the bone plate 100E. The bone screw 300 may also include bone threads 304, which are configured to penetrate and engage, e.g., bone.

Figure 9A:
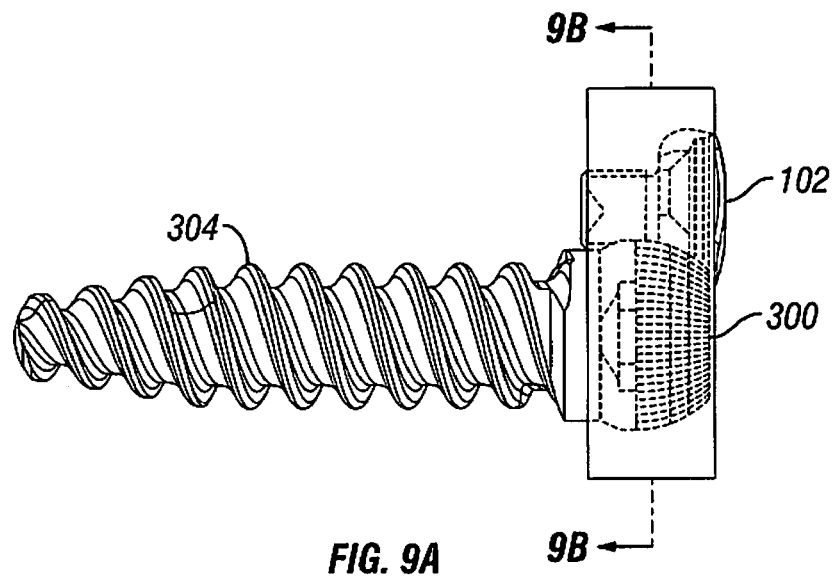
FIG. 9A shows a side view of a bone plate with a set screw and a notched-head bone screw.
Figure 9B:
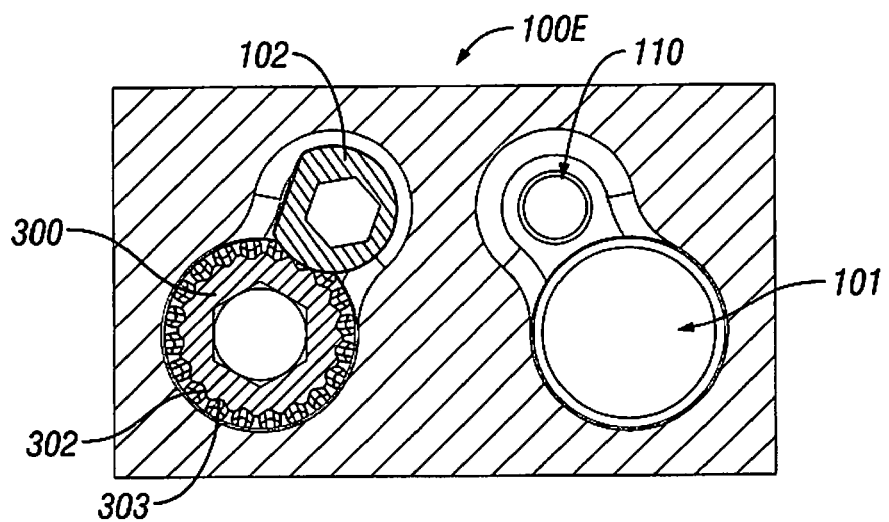
FIG. 9B is a cutaway view taken along line B-B in FIG. 9A.

FIG. 9A shows a side view of the plate 100E with a set screw 102 and bone screw 300. FIG. 9B is a cutaway view taken along line B-B. FIG. 9B shows how the set screw 102 may interface with the ridges 302 and notches 303 of the head portion of the bone screw 300. This interaction may substantially or completely prevent rotation of the bone screw 300 when the construct, including bone plate 100E, is subjected to normal biomechanical forces within the body.

Various systems, devices and methods for aligning a plate with a spacer body are now provided. While the systems, devices and methods are described with respect to a plate 100 having ridged features as discussed above, they are not limited to this particular type of plate, and can be used to align various other types of plates with a spacer body.

Figure 12:
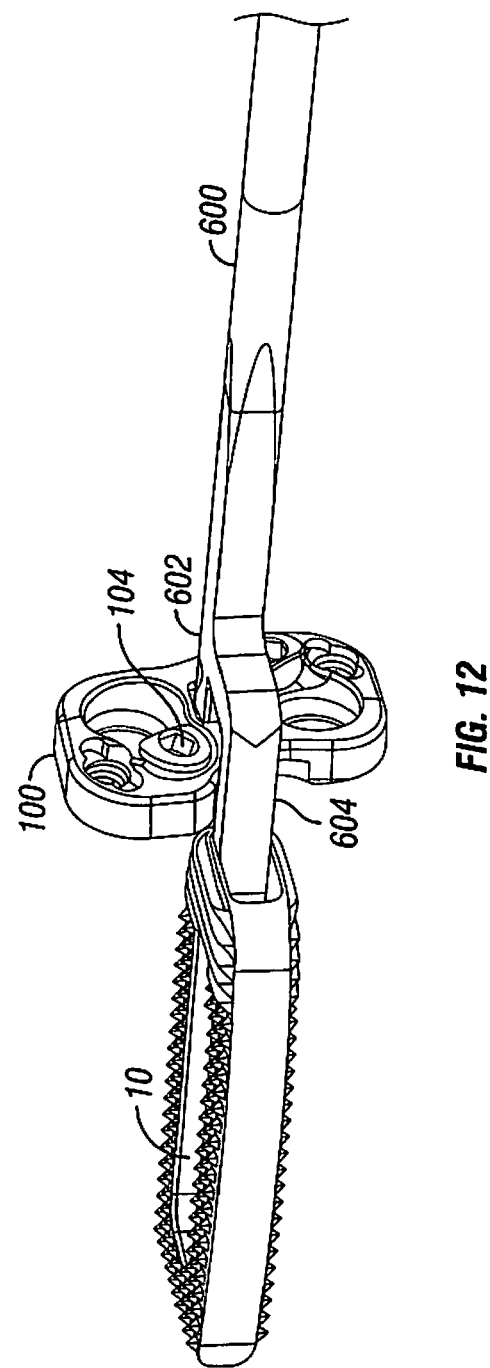
FIG. 12 shows an additional alternative system including a tool for aligning a bone plate with a spacer body.

FIGS. 10-12 show various systems that allow a plate 100 to be guided and aligned with a spacer body 10. In some embodiments, a spacer body 10 is already inserted and positioned at a location within a spine. The systems described herein provide a convenient means to guide a plate 100 through a small incision path toward the spacer body 10. Advantageously, the plate 100 can be guided through an incision and a small opening (e.g., formed by a retractor), until it is positioned and fixed adjacent the spacer body 10.

FIG. 10 shows a system including a tool for aligning a bone plate with a spacer body. The system includes a spacer body 10, a bone plate 100 having fasteners 300, and a guide 400 for aligning the bone plate with the spacer body. An optional keying tool 500 is also provided to assist in preventing rotation of the plate 100 with respect to the spacer body 10, as discussed further below.

The spacer body 10 includes a superior surface 22 and an inferior surface 26 that are configured to contact upper and lower vertebrae, respectively. In some embodiments, the surfaces can include surface protrusions, such as teeth or ridges, to assist in gripping the surfaces of the vertebrae. An opening 15 can be formed through the spacer body. The opening 15 can be configured to receive bone material, such as bone graft material, to facilitate fusion of the spacer body 10 within the vertebrae. In some embodiments, the opening 15 is substantially rectangular in shape, while in other embodiments, the opening 15 is more circular.

Figure 14:
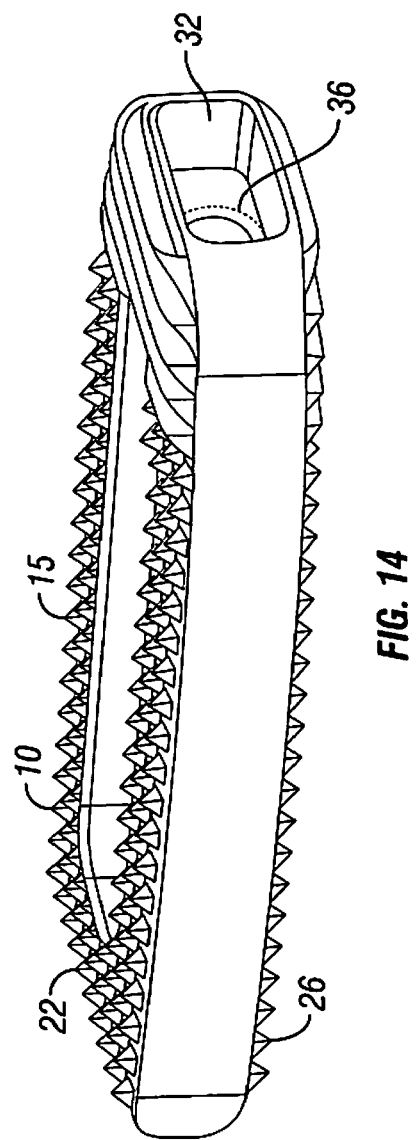
FIG. 14 shows a spacer body.

In some embodiments, the spacer body 10 can also include a recess 32 formed on an anterior and/or posterior face. As shown in FIG. 14, the recess 32 can be circular, rectangular or various other configurations. The recess 32 can transition into an aperture 36 that is smooth or threaded. In some embodiments, the aperture 36 is configured to receive a portion of a guide member 400, as discussed in more detail below.

The spacer body 10 can be inserted in between two vertebrae. Once the spacer body 10 is inserted in a desired position, a bone plate 100 can be provided through an incision and can be placed adjacent the spacer body 10.

The bone plate 100 can include any of the features discussed above, including one or more holes 101 for receiving fasteners 300 and an additional central hole 104 for receiving a guide 400. The bone plate 100 can also include a ridged perimeter. In some embodiments, the bone plate 100 is configured to be placed adjacent to the spacer body 10, such that it can be fixed to upper and lower vertebrae via fasteners 300. While in some embodiments, the bone plate 100 is attached to the spacer body 10, in other embodiments, the bone plate 100 is not attached to the spacer body 10. As shown in FIG. 10, in some embodiments, the bone plate 100 is placed perpendicularly at about a 90-degree angle relative to the spacer body 10. In other embodiments, the bone plate 100 can be placed at a different angle from 90-degrees relative to the spacer body 10. In order to place the bone plate 100 in a desired position, the system includes a unique guide 400 that can guide the bone plate 100 through an incision path.

The novel guide 400 can include a first substantially rigid portion 402 and a second more flexible portion 408. In some embodiments, the rigid portion 402 can be of a different material from the flexible portion 408. For example, in some embodiments, the rigid portion 402 can comprise a metal such as stainless steel that is operably attached to a flexible portion 408 comprising a nitinol wire. The stainless steel rigid portion 402 can advantageously comprise a threaded portion 414 (shown in FIG. 10) that allows the guide 400 to be attached to the spacer body 10. In some embodiments, the rigid portion 402 comprises a material other than stainless steel, such as PEEK, cobalt chrome, nitinol, TAV, CP (titanium) or other compatible biomaterial.

The flexible portion 408 of the guide 400 can extend outwardly from the rigid portion 402 and outwardly from an incision. When the flexible portion 408 extends outwardly from the incision, a plate 100 can be delivered down the flexible portion. In some embodiments, the flexible portion 408 advantageously allows a plate 100 to be inserted at a non-perpendicular angle to retractor blades, thereby decreasing the size of the aperture needed to insert the plate therethrough. In some embodiments, the flexible portion 408 is fastened into the rigid portion 402. In some embodiments, an epoxy filler can be used to secure the flexible portion 408 to the rigid portion 402. The flexible portion 408 can be comprised of various materials, including but not limited to nitinol. In addition, in some embodiments, the flexible portion 408 can comprise a stainless steel or titanium cable.

Together, the flexible portion 408 and rigid portion 402 can be viewed either as a single guide member, or as multiple guide members secured together. In some embodiments, the length of the rigid portion 402 can be between about 2 and 25 percent, or between about 5 and 10 percent, of the length of the entire guide 400 having a flexible portion 408 and a rigid portion 402 In some embodiments, the length of the rigid portion 402 can be between about 15 and 45 mm, or about 30 mm. The length of the flexible portion 408 can be between about 350 and 550 mm, or about 450 mm. In some embodiments, the rigid portion is just long enough to engage a plate 100 when it is seated on the vertebral bodies and just long enough for a tool to connect to it to insert it and remove it after the plate 100 has been placed Advantageously, these dimensions allow the flexible portion 408 to extend outwardly from an incision, while maintaining the rigid portion 402 near the inserted spacer body 10.

In operation, after the spacer body 10 has been inserted into a desired disc space, the guide 400 can be attached to the spacer body 10. The bone plate 100 can be inserted over the guide 400 via the central hole 104, where it can travel over the flexible portion 408 and subsequently, over the rigid portion 402 of the guide 400. In some embodiments, the central hole 104 can be non-circular (e.g., square or rectangular) and/or with edges, thereby advantageously minimizing rotation of the plate 100 as it travels along the guide 400. Advantageously, while the bone plate 100 is delivered over the flexible portion 408, the bone plate 100 is capable of assuming a number of different orientations via tilting and manipulation, thereby allowing a minimally invasive delivery (e.g., through retracted tissue). After passing the flexible portion 408 of the guide 400, the plate 100 traverses over the rigid portion 402 of the guide 400. The rigid portion 402 of the guide 400 advantageously helps to align the plate 100 with the spacer body 10. Once the plate 100 is in place adjacent the spacer body 10, it can be secured to vertebrae via fasteners 300.

Optionally, a keying tool 500 (shown in FIG. 10) can be provided to assist in preventing rotation of the plate 100 with respect to the spacer body 10. The keying tool 500 comprises a sleeve that is configured to slide over the guide 400 and through the central hole 104. In some embodiments, the keying tool is made of a biocompatible metal, such stainless steel or titanium. In some embodiments, the keying tool 500 can have a shape that corresponds to the shape of the central hole 104 and/or the shape of the recess 32 in the spacer body 10. By having a corresponding shape, this advantageously prevents rotation of the plate 100 relative to the spacer body 10. In some embodiments, the keying tool 500 can have a non-circular shape and/or shape with edges that corresponds with the shape of the central hole 104. In some embodiments, the keying tool 500 is slightly smaller than the central hole 104 of the plate 100, thereby advantageously allowing for a minimal amount of toggle and misalignment of the parts. While the keying tool 500 is shown with respect to the system in FIG. 10, it can also be used with the systems shown in other embodiments. In addition, when the keying tool 500 is not inserted into a recessed area of the spacer, it can be used to rotate the plate to any angle desired. In an alternative embodiment, the keying tool 500 can be made cylindrical to take up slop between the rigid portion of the guide 400 and the plate 100, but still allow the plate 100 to be rotated thereon.

FIG. 11 shows an alternative system including a tool for aligning a bone plate with a spacer body. Like the system in FIG. 10, the present system includes a spacer body 10, a plate 100 and a guide 400 having a flexible portion 408 and a rigid portion 402. However, rather than having a screw member 414 attached to the rigid portion 402, the present guide 400 has a rigid portion 402 including a pressure press-fit end 419 that holds within the spacer body 10. The shape of the pressure press-fit end 419 advantageously correlates to the shape of the plate recess 32 (shown in FIG. 14) such that when the plate 10 is slid over the rigid portion 402 of the guide 400, it is guided and keyed into a proper position. The plate 100 is thus held in line with the spacer body 10.

In some embodiments, the recess 32 of the spacer body 10 can be shaped and dimensioned to allow movement of the press-fit end 419. For example, the recess 32 can have a slightly larger length than the press-fit end 419 of the guide 400, thereby allowing some side translation of the guide 400. The guide 400 can thus be translated off-center, thereby allowing both center and off-center placement of the plate 100 relative to the spacer body 10. This advantageously allows a surgeon to place the plate 100 in various locations relative to the spacer body 10.

FIG. 12 shows an additional alternative system including a tool for aligning a bone plate with a spacer body. The system comprises a spacer body 10, a plate 100 and an alternative keying tool 600 having a distinct design.

Once the plate 100 has been positioned adjacent the spacer body 10 (e.g., via a guide 400 as discussed above), a keying tool 600 can be provided. In some embodiments, the keying tool 600 is provided on its own, while in other embodiments, the keying tool 600 is cannulated and extends over the guide to a desired surgical location. In some embodiments, the keying tool 600 can comprise a fork-member having one or more fingers, prongs or tines to assist in holding the position of the plate 100 relative to the spacer body 10. One or more of the prongs can have a shape (e.g., non-circular) that corresponds with the shape of the central hole 104. As shown in FIG. 12, the keying tool 600 can comprise at least two prongs 602 and 604. First prong 602 extends through a central hole 104 of the plate 100 and into the recess 32 of the of the spacer body 100. Advantageously, the shape of the first prong 602 substantially correlates with the shape of the central hole 104 of the plate in order to properly align the plate and/or prevent it from rotating. Second prong 604 is parallel and off-set axially from first prong 602, and can also extend into the recess 32 of the spacer body if desired. In some embodiments, the first prong 602 and the second prong 604 are of different lengths such that one prong can extend into the recess 32 of the spacer body, while the other does not extend into the recess 32 of the spacer body. In addition, in some embodiments, the spacer body recess 32 is dimensioned to allow translation of the keying tool 600 therein.

Figure 13A:
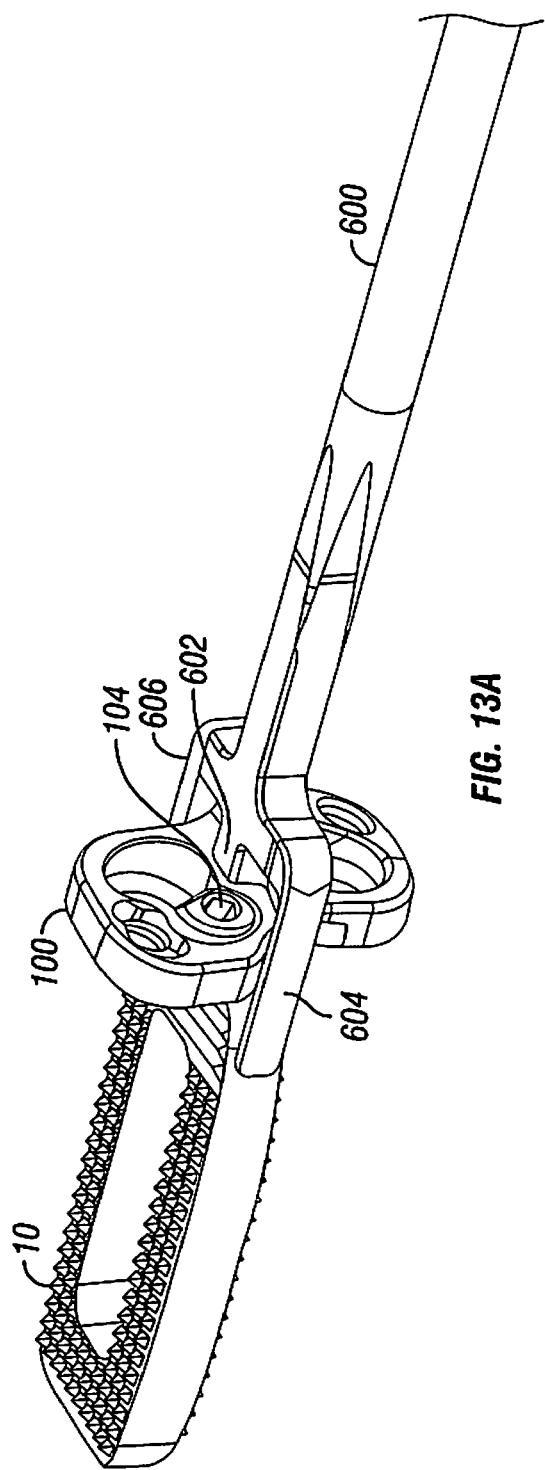
FIG. 13A shows an additional alternative system including a tool for aligning a bone plate with a spacer body.

FIG. 13A shows an additional alternative system including a tool for aligning a bone plate with a spacer body. Like the system in FIG. 12, the present system includes a spacer body 10, a plate 100 and a keying tool 600. However, the keying tool 600 in FIG. 13A includes three prongs 602, 604 and 606. First prong 602 extends through the central hole 104 of the plate 100 and into the recess 32 of the spacer body 10. The shape of the first prong 602 substantially correlates with the shape of the central hole 104 of the plate 100 so that it is advantageously prevented from rotating relative to the spacer body 10. Second prong 604 and third prong 606 extend parallel to the first prong 602. In some embodiments, as shown in FIG. 13A, the second prong 604 and third prong 606 can rest against the outside surface of the spacer body 10, thereby advantageously providing additional stabilization to the system. In some embodiments, sides of the spacer body 10 can include recessed slots that can allow one or more of the prongs (e.g., prongs 604, 606) to slide into therein, thereby further helping to stabilize the position of the plate relative to the spacer.

Figure 13B:
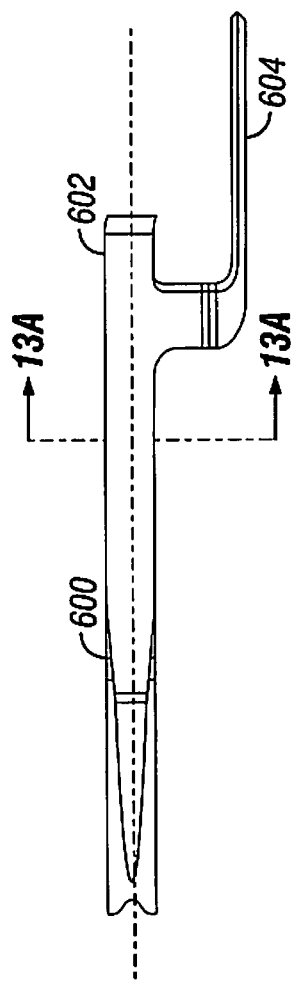
FIG. 13B shows an alternative tool for aligning a bone plate with a spacer body.

FIG. 13B shows an additional alternative tool for aligning a bone plate with a spacer body. The keying tool 600 includes two prongs 602 and 604. In some embodiments, the first prong 602 can be received through a central hole of the plate 100, while the second prong 604 can extend along a side of the plate 100 and/or spacer 10. As shown in FIG. 13B, the two prongs can have different lengths.

Any of the keying tools shown in FIGS. 10, 12, 13A and 13B can be cannulated to slide over the surface of the guide comprising the rigid and flexible members. In some embodiments, the cannulated portion of the keying tools is large enough to accept additional tools other than the guide.

Various methods are provided for inserting the systems described above. In some embodiments, a surgeon will form an incision and a path to a disc space. A spacer body, such as one with a ridged perimeter, can be delivered and inserted into the disc space. A guide, such as one having a rigid portion and a flexible portion, can be delivered and operably connected to the spacer body. A plate can then be delivered over the guide, first over the flexible portion and then over the rigid portion. Once the plate is delivered to a desired area adjacent the spacer body, the plate can secured to vertebrae using one or more fasteners. Optionally, before and/or after securing one or more fasteners of the plate into a vertebral body, a keying tool can be provided. In some embodiments, the keying tool comprises a cannula that fits over the guide and through a central hole in the plate. The keying tool advantageously helps to prevent rotation of the plate relative to the spacer body prior to securing the system. Once the spacer body and plate are secured (or temporarily held in place by temporary fixation pins), the guide and/or keying tool can be removed.

To assist in delivering a plate to a location adjacent a spine, different insertion devices can be provided as discussed herein. These novel insertion devices advantageously afford a surgeon an effective instrument for delivering the plates while maintaining a slim profile to allow surgeons to see a surgical site.

FIG. 15A shows a top perspective view of a plate insertion device for delivering a plate to a desired location adjacent the spine. FIG. 15B shows a perspective view of a distal portion of the plate insertion device of FIG. 15A grasping a plate.

The plate insertion device 300 comprises a number of components including a sleeve 320 extending to a proximal portion 340 of the device that serves as a handle. A grasping member 310 for securely holding a plate 100 extends from a distal opening of the sleeve 320. The grasping member 310 comprises a pair of parallel jaws 311. Hinged tips 312 having extension portions 314 extend from the parallel jaws 311.

The grasping member 310 of the device 300 comprises a pair of parallel jaws 311. The parallel jaws 311 can be configured to contract and expand. In some embodiments, when the parallel jaws 311 are in a contracted configuration, the jaws 311 can be slid into the body of the sleeve 320. In some embodiments, when the parallel jaws 311 are in an expanded configuration, the jaws 311 extend outward from the body of the sleeve 320. The parallel jaws 311 can be spring-loaded. In some embodiments, the parallel jaws 311 are configured to hold a side of a plate 100 (as shown in FIG. 15B). In other embodiments, the parallel jaws 311 can hold posterior and/or anterior surfaces, or upper and lower surfaces of the plate 100.

Hinged tips 312 are connected to the parallel jaws 311. The hinged tips 312 comprise curved fingers that can rotate and/or actuate around one or more pivot pins 313 (shown in FIG. 15B). In some embodiments, rotation of the hinged tips 312 can be controlled by an actuation member. The hinged tips 312 are advantageously configured to pivot and allow a large range of rotation in a very small arc, such that the device 300 can be delivered with a plate 100 through a very small opening. Advantageously, the arms of the hinged tips 312 are offset from the pivot point, thereby allowing the use of center hole in the plate 100. Moreover, the hinged tips 312 advantageously provide a surgeon with flexibility in placing the plate 100 in a desired location. In some embodiments, the hinged tips 312 are able to hold a plate 100 about or completely perpendicular to the instrument (e.g., the longitudinal axis of the sleeve 320) and rotate it up to the point that it is almost parallel to the sleeve 320. A stop formed on the hinged tips 312 can assist in prevent over-rotation of the plate. By providing such a rotational feature, this advantageously makes it easier to cause the plate 100 to begin rotating when inserting it and pushing it against the surface of a vertebral body in some instances.

Extension portions 314 extend inwardly (e.g., to face a mid-line of the device 300) from the hinged tips 312. These extension portions 314 are advantageously configured to securely grip a recess formed in the body of the plate 100, as shown in FIG. 15B.

The parallel jaws 311 and hinged tips 312 are configured to encompass an opening 318 in the grasping member 310. Advantageously, when a plate 100 is secured to grasping member 310 (as shown in FIG. 15B), the opening 318 in the grasping member 310 provides a means to visualize the plate 100. In addition, in some embodiments, the opening 318 in the grasping member 310 can be substantially aligned with the central hole 104 of the plate 100. In this situation, when the opening 318 is aligned with the central hole 104 such that the opening 318 is in front of the cross-member between the tips 312, this advantageously allows the plate 100 to be inserted over a flexible guide while it is being held by the plate insertion device 300. As the grasping member 310 holds the plate 100 via recesses on its side body, the central hole 104 can remain in use such that a guide (such as the combined flexible and rigid guide discussed above) can still be used through the central hole 104. Thus, the plate insertion device 300 can advantageously be used with a guide that extends through the hole 104 of the plate 100.

The grasping member 310 can extend outwardly from an opening in the sleeve 320. In some embodiments, the sleeve 320 extends a majority of the length of the device 300. The sleeve 320 can include a narrow mid-section that becomes slightly wider near its proximal end to form a proximal handle portion 340. The slim design of the sleeve 320 and its handle proximal handle portion 320 advantageously helps to maintain the sightlines of the surgeon through the use of the instrument. In some embodiments, the diameter of the sleeve 320 is between about 5 and 15 mm, or between about 8 and 12 mm The most proximal end of the sleeve 320 can be in contact with an actuation knob 342, which can be configured to open and close the arms of the grasping member 310. In some embodiments, the actuation knob 310 can be connected to the parallel jaws 311 via an internal rod with a threaded end. When the knob 310 is turned, it pulls or pushes the jaws into or out of the sleeve 320, thereby causing expansion or contraction.

Figure 16A:
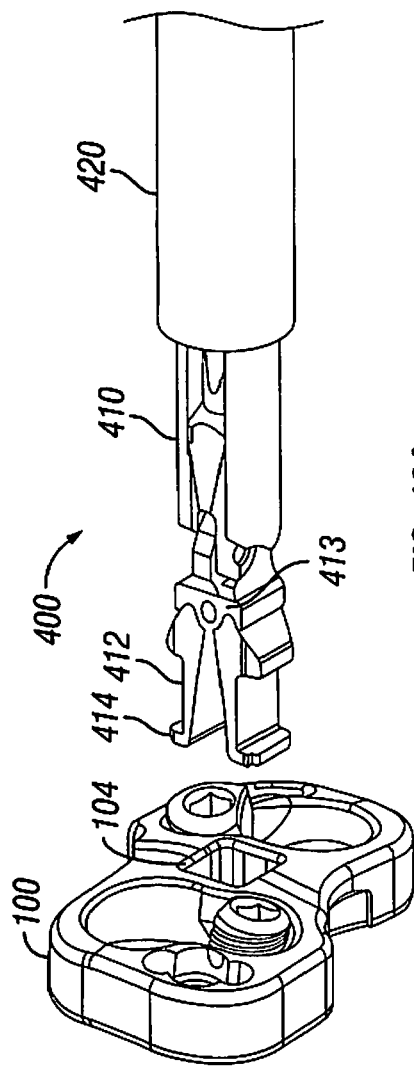
FIG. 16A shows a top perspective view of an alternative plate insertion device for delivering a plate to a desired location adjacent the spine.
Figure 16B:
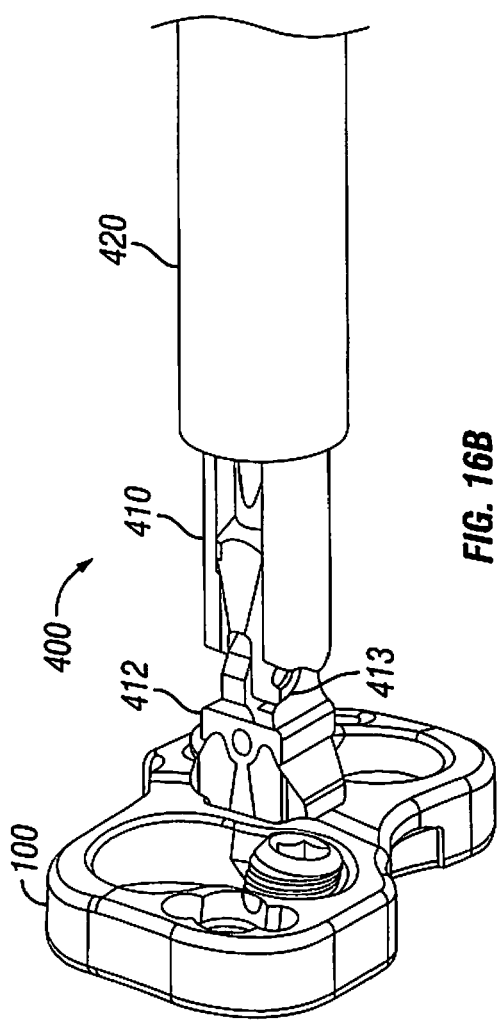
FIG. 16B shows a perspective view of a distal portion of the plate insertion device of FIG. 16A grasping a plate.

In some embodiments, the actuating knob 342 can have external surface roughening, such as ribbing, a knurled surface, etc. so as to be conveniently gripped by a surgeon. In some embodiments, rotating the actuating knob 342 closes the parallel jaws 311 such that they securely grip a surface of the plate 100. Rotating the actuating knob 342 in an opposite direction will open the parallel jaws 311 to release the plate 100 therefrom. As the actuating knob 342 is controlled by a smooth controlled rotation, the parallel jaws 311 can open or close in a continuous manner, thereby gripping or releasing the plate 100 in an accurate, controlled manner. In some embodiments, the parallel jaws 311 are advantageously spring-loaded to provide a secure grip on the plate 100. In this situation, the spring can act to open the parallel jaws and the sleeve can act to close the parallel jaws as they are pulled into the sleeve FIGS. 16A-D show different views of an alternative plate insertion device for delivering a plate to a desired location adjacent the spine. The device 400 includes a sleeve 420 and a grasping member 410 that extends from an opening of the sleeve 420. A distal portion of the grasping member 410 includes an articulating linking member 413 configured to rotate and articulate distal extension arms 412. The extension arms 412 include outward protrusions 414 that help to secure a plate 100, as shown in FIGS. 16B and 16C.

Unlike the grasping member 310 in FIG. 15A, the grasping member 410 in FIG. 16A is configured to attach to the central hole 104 in the plate 100 if desired. One skilled in the art will appreciate that holes other than the central hole 104 of the plate 100 can also be used for attachment by grasping member 410. In some embodiments, the grasping member 410 includes an articulating linking member 413 that is capable of articulating and rotating distal extension arms 412 (e.g., between 0 and 90 degrees). Articulation of the linking member 413 can be performed via rotation of a knob, such as the one shown on the proximal portion of the device 300 in FIG. 15A. When the linking member 413 is rotated, this also rotates arms 412. The arms 412 can be attached to the plate via protrusions 414 that extend outwardly (e.g., away from a midline of the device 400) from the arms 412.

Advantageously, as the grasping member 410 of the device 400 includes arms 412 that are capable of gripping a central hole of the plate 100 of minimal diameter, the device 400 is extremely small in width and thus capable of being used through very small incisions. After entering through a small incision, the device 400 advantageously provides the ability to control the articulation of the plate 100 in a very controlled manner.

It will be apparent to one skilled in the relevant arts that any of the above-described modifications may be combined. For example, a bone plate may include a sharp, peripheral ridge to enhance stability of the construct; optional spikes for further enhancing stability; and notched-head bone screws to prevent rotation of the screws inside the body. Other combinations are possible and contemplated. A bone plate or other construct or instrumentation may utilize any combination of the above-described enhancements without departing from the spirit and scope of the specification, including the attached claims.

While the disclosure has been described in terms of exemplary aspects, those skilled in the art will recognize that the disclosure can be practiced with modifications in the spirit and scope of the appended claims. These examples given above are merely illustrative and are not meant to be an exhaustive list of all possible designs, aspects, applications or modifications of the disclosure.

What is claimed is:

1. A surgical system comprising:
   a spacer body having an anterior surface and a recess formed in the anterior surface;
   a bone plate attachable to the spacer body and having a central hole;
   a tool configured to pass entirely through the central hole of the bone plate and into the recess to align the bone plate to the spacer body,
   wherein the recess of the spacer body is larger than a distal end of the tool such that the distal end is allowed to translate laterally within the recess
   wherein the spacer body comprises a superior surface and an inferior surface, and an opening that extends through the superior surface and inferior surface,
   wherein the spacer body further comprises a posterior surface, wherein the anterior surface and the posterior surface are disposed between the superior surface and inferior surface
   wherein the recess in the anterior surface of the spacer body transitions into a smaller opening therein
   wherein the bone plate comprises an upper fastener and a lower fastener extending therethrough.

2. The surgical system of claim 1, wherein the tool for aligning the bone plate comprises a guide.

3. The surgical system of claim 2, wherein the guide comprises a rigid portion and a flexible portion.

4. The surgical system of claim 3, wherein the rigid portion comprises a metal and the flexible portion comprises nitinol wire.

5. The surgical system of claim 3, wherein the flexible portion is fastened into the rigid portion.

6. The surgical system of claim 1, further comprising:
   a keying tool configured to stabilize a position of the bone plate relative to the spacer body.

7. A surgical system comprising:
   a spacer body having an anterior surface and a recess formed in the anterior surface;
   a bone plate attachable to the spacer body, wherein the bone plate comprises a first hole for receiving a first bone fastener and a second hole for receiving a second bone fastener and a central hole; and
   a tool configured to pass entirely through the central hole of the bone plate and into the recess to align the bone plate to the spacer body, wherein the recess of the spacer body is larger than a distal end of the tool such that the distal end is allowed to translate laterally within the recess wherein the spacer body comprises a superior surface and an inferior surface, and an opening that extends through the superior surface and inferior surface, wherein the spacer body further comprises a posterior surface, wherein the anterior surface and the posterior surface are disposed between the superior surface and inferior surface, wherein the recess in the anterior surface of the spacer body transitions into a smaller opening therein wherein the bone plate comprises an upper fastener and a lower fastener extending therethrough.

8. The surgical system of claim 7, wherein the tool for aligning the bone plate comprises a guide.

9. The surgical system of claim 8, wherein the guide comprises a rigid portion and a flexible portion.

10. The surgical system of claim 9, wherein the rigid portion comprises a metal and the flexible portion comprises nitinol wire.

11. The surgical system of claim 9, wherein the flexible portion is fastened into the rigid portion.

12. The surgical system of claim 7, further comprising:
a keying tool configured to stabilize a position of the bone plate relative to the spacer body.

* * * * *